United States Patent [19]

Schulz, Jr. et al.

[11] Patent Number: 4,783,543
[45] Date of Patent: Nov. 8, 1988

[54] PROCESS TO PRODUCE SILYL KETENE ACETALS

[75] Inventors: William J. Schulz, Jr.; John L. Speier, both of Midland, Mich.

[73] Assignee: Dow Corning Corporation, Midland, Mich.

[21] Appl. No.: 123,850

[22] Filed: Nov. 23, 1987

[51] Int. Cl.$^4$ .............................................. C07F 7/18
[52] U.S. Cl. ................... 556/446; 556/470
[58] Field of Search ........................ 556/470, 446

[56] References Cited

U.S. PATENT DOCUMENTS

| | | | |
|---|---|---|---|
| 4,377,706 | 3/1983 | Hallgren | 556/470 X |
| 4,414,372 | 11/1983 | Farnham et al. | 526/190 |
| 4,417,034 | 11/1983 | Webster | 526/190 |
| 4,482,729 | 11/1984 | Ishikawa | 556/446 |
| 4,508,880 | 4/1985 | Webster | 526/190 |
| 4,582,924 | 4/1986 | Ishikawa et al. | 556/470 X |

FOREIGN PATENT DOCUMENTS 0184692 6/1986 European Pat. Off. ..... 556/470 UX

OTHER PUBLICATIONS

Slougui et al., "Syn. Comm.", 17(1), pp. 1–11, 1987.
Petrov et al., J. Gen. Chem. (USSR), 29 (1959), pp. 2896–2899.
Ainsworth et al., J. Organometallic Chem. 46 (1972), pp. 59–71.
Kita et al., Tetrahedron Letters, 24:12 (1983), pp. 1273–1276.
Brown, J. Org. Chem., 39:9 (1974), pp. 1324–1325.
Kuo et al., Chemical Communications, (1971), pp. 136–137.
Ojima et al., J. Organometallic Chem., 111(1976), pp. 43–60.
Howe et al., J. Organometallic Chem., 208(1981), pp. 401–406.
Yoshii et al., Chem. Pharm. Bull., 22(1974), pp. 2767–2769.
Chen et al., J. Am. Chem. Soc., 94:11 (1972), pp. 4037–4038.
Ruhlmann, Synthesis (1971), pp. 236–253.
Ruhlmann et al., J. Organometal Chem., 27(1971), pp. 327–332.

Primary Examiner—Paul F. Shaver
Attorney, Agent, or Firm—Carl A. Yorimoto

[57] ABSTRACT

A process for the preparation of silyl ketene acetals of the formula,

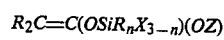

$$R_2C=C(OSiR_nX_{3-n})(OZ)$$

or

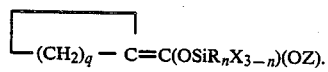

The process comprises contacting an alpha-ester of a carboxylic acid with an alkali metal in the presence of an excess of an organohalosilane, wherein the alpha-ester has the formula,

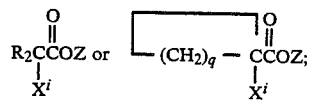

and the organohalosilane has the formula,

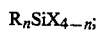

$$R_nSiX_{4-n};$$

and facilitating reaction among the alpha-ester, the alkali metal, and the organochlorosilane to form the silyl ketene acetal and an alkali metal halide or an alkali metal alkoxide.

23 Claims, No Drawings

PROCESS TO PRODUCE SILYL KETENE ACETALS

BACKGROUND OF THE INVENTION

This invention relates to a process for the manufacture of silyl ketene acetals (SKA). More specifically, this invention relates to a process for producing silyl ketene acetals from the reaction of esters of alpha-substituted carboxylic acids with an alkali metal in the presence of an organohalosilane.

For the purposes of the instant invention, esters of alpha-substituted carboxylic acids will be referred to as "alpha-esters"; as a further example, esters of carboxylic acids substituted in the alpha-position with halogen will be referred to as "alpha-haloesters." Likewise, esters of beta-substituted carboxylic acids will be referred to as "beta-esters."

The first reference to preparation of silyl ketene acetals (SKA) was in the late-1950's by Petrov et al., *J. Gen. Chem. (USSR)*, 29(1959), pp. 2896-2899. This reference and most of the other references to the art deal with chemical species of the general formula,

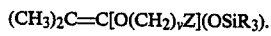
$(CH_3)_2C=C[O(CH_2)_vZ](OSiR_3)$.

R is selected from a group consisting of alkyl groups, aryl groups, alkaryl groups, and substituted alkyl, aryl, and alkaryl groups; v has a value of 0, 1 or more; Z is such groups as alkyl, alkenyl, aryl, alkaryl; any of these groups containing one or more functional groups, such as ether oxygen atoms, thio groups, organosiloxy groups, which are unreactive under silylating conditions. These organosilane intermediates are of value because of the ability to further react the SKA to prepare organic compounds which would be difficult to synthesize by other means. A very recent application is the use of the SKA as acrylate polymerization initiators. This concept known as Group Transfer Polymerization (GTP) was developed by DuPont and is disclosed in three U.S. patents—U.S. Pat. No. 4,414,372, Farnham et al., issued Nov. 8, 1983; U.S. Pat. No. 4,417,034, Webster, issued Nov. 22, 1983; and U.S. Pat. No. 4,508,880, Webster, issued Apr. 2, 1985.

Four procedures for preparing silyl ketene acetals are known in the art. The first general route to SKA is the reaction of an ester of a carboxylic acid with an appropriate metal reagent to form a metal enolate ion and subsequent reaction of the enolate ion with an organochlorosilane. Ainsworth et al., *J. Organometallic Chem.*, 46(1972), pp. 59-71, describe the preparation of an SKA via the reaction of esters of carboxylic acids with lithium diisopropylamide, followed by reaction with trimethylchlorosilane, Kita et al., *Tetrahedron Letters*, 24:12 (1983), pp. 1273-1276, discloses a similar procedure to prepare bifunctional SKA, Brown, *J. Org. Chem.*, 39:9(1974), pp. 1324-1325, describes the preparation of metal enolate ions by reacting potassium hydride in tetrahydrofuran with a carbonyl compound, followed by reaction with excess triethylamine and trimethylchlorosilane.

Kuo et al., *Chemical Communications*, (1971), pp. 136-137, discloses the preparation of silyl ketene acetals of the formula,

$R^1R^2C=C[OSi(CH_3)_3]_2$, wherein $R^1$ and $R^2$ are hydrogen, methyl, t-butyl, and phenyl, The silyl ketene acetal is prepared by the reaction of the corresponding carboxylic acid or silyl ester of a carboxylic acid in contact with lithium diisopropylamide, trimethylchlorosilane, and tetrahydrofuran. Yields of the desired silyl ketene acetal of from 29 to 85 percent are disclosed. Kuo et al., are silent as to whether or not the yield figures disclosed are calculated by analysis or physical isolation and separation.

In a second general procedure, silyl ketene acetals are prepared by the hydrosilation of esters of carboxylic acid with organohydrosilanes. Petrov et al., *J. Gen. Chem. (USSR)*, 29(1959), pp. 2896-2899, described the platinumcatalyzed reaction of methyl methacrylate with triethylsilane. Ojima et al., *J. Organometallic Chem.*, 111(1976), pp. 43-60, studied the use of tris(triphenylphosphine)rhodium chloride as a catalyst. Howe et al., *J. Organometallic Chem.*, 208(1981), pp. 401-406, and Yoshii et al., *Chem. Pharm. Bull.*, 22(1974), pp. 2767-2769, describe yields of 70-75% SKA from the reaction of $(C_2H_5)_3SiH$ and methyl methacrylate using organophosphorous complexes of rhodium as a catalyst. Quirk et al., in European Patent Application No. 0184692, published June 18, 1986, discloses o-silylated ketene acetals and enol ethers and a process for their preparation from the reaction of acrylate esters and silanes or siloxanes in the presence of a rhodium catalyst.

In a third procedure Ishikawa et al., in U.S. Pat No. 4,482,729, issued Nov. 13, 1984, describes the preparation of a fluoroalkyl silyl ketene acetal by the reaction of a fluorinated carboxylic acid ester with trimethylsilyl trifluoromethanesulfonate.

The fourth procedure involves the alkali metal reduction of disubstituted malonates in the presence of trimethylchlorosilane to produce a silyl ketene acetal, Kuo et al., *Chemical Communications*, (1971), pp. 136-137; and *J. Am. Chem. Soc.*, 94:11 (1972), pp. 4037-4038, disclose the preparation of silyl ketene acetals of the formula,

$R^1R^2C=C(OR^3)OSi(CH_3)_3$, from the reaction of a dialkyl dialkylmalonate with trimethylchlorosilane in the presence of sodium metal, wherein the $R^1$ and $R^2$ are methyl; ethyl, or phenyl; and $R^3$ is methyl or ethyl.

Ruhlmann, *Synthesis* (1971), pp. 236-253, particularly Section 1.1.5.2, discusses the reactions of alpha- and beta-haloesters of carboxylic acids with sodium and trimethylchlorosilane, Ruhlmann points out that the primary reaction of the beta-haloesters is the conversion of the ester to their corresponding silyl cyclopropanone ketals, the betahaloesters having the formula,

and the ketals having the formula,

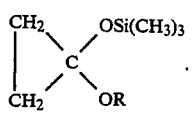

Ruhlmann shows that the alpha-haloesters,

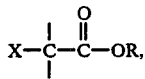

follow a more complicated route. Ruhlmann points out that esters such as methyl chloroacetate yield almost exclusively the C-silylated ester,

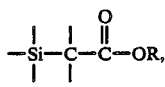

which undergoes acyloin condensation to yield tetrasilylated products—in the case of methyl chloroacetate, the product is 1,4-bis(trimethylsilyl)-2,3-bis(trimethylsilyloxy)-2-butene. Only in one example did the author cite a case in which the predominant product was a silyl ketene acetal. This case was the reaction of ethyl 2-bromopropionate with trimethylchlorosilane and sodium in diethyl ether. The reported yield was 75% silyl ketene acetal. Ruhlmann's example involved an ester in which the halogen atom is bonded to a *secondary* carbon atom, and not a *tertiary* carbon atom as taught by the instant invention. Ruhlmann's example was carried out in the examples, infra. The results of this example indicated that while a silyl ketene acetal was formed, there were also substantial quantities of both the C-silylated ester and the acyloin condensation product. The inventors have found unexpectedly that alpha-esters in which a halogen atom or alkoxy group is bound to a *tertiary* carbon atom react with alkali metals in the presence of excess organohalosilanes to yield silyl ketene acetals almost exclusively. There is virtually no acyloin condensation product.

Ruhlmann et al., *J. Organometal. Chem.*, 27(1971), pp. 327–332, shows that a minor amount of silyl ketene acetals could be produced from the reaction of alkyl phenylacetates with sodium in the presence of trimethylchlorosilane. The yields of silyl ketene acetal were low, 2–8%; benzylsilanes and bissiloxyalkenes were the primary products.

Nowhere does prior art demonstrate or suggest the general preparation of silyl ketene acetals in high yields from the reaction of an alkali metal and an alpha-ester of a carboxylic acid, an ester in which a halogen atom or an alkoxy group is bonded to a *tertiary* carbon atom, in the presence of an organohalosilane.

SUMMARY OF THE INVENTION

The instant invention is based upon the unexpected finding that silyl ketene acetals having the formula, $$R_2C=C(OSiR_nX_{3-n})(OZ)$$

or

can be prepared from the reaction of an alpha-ester of a carboxylic acid,

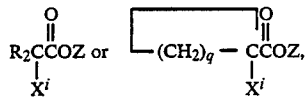

with an alkali metal in the presence of an excess of organohalosilane,

The details of these chemical structures and the instant invention are presented, infra.

The objective of the instant invention is to provide an economical new route for the preparation of a wide range of silyl ketene acetals that can be isolated and separated at high purity.

The instant invention has several advantages over the known methods for preparing SKA. Comparing the instant invention to the route in which SKA are prepared by the reaction of an ester of a carboxylic acid with an appropriate metal reagent to form a metal enolate ion and subsequent reaction of the enolate ion with an organochlorosilane, the instant invention has the advantage of lower raw material costs. The art teaches the preparation of metal enolate ions via the reaction of a carbonyl compound with a metallic reagent such as lithium diisopropylamide or potassium hydride. Both of these metallic reagents are much more costly than the alkali metal utilized in the instant invention. The reactions can also include additional reagents such as triethylamine. The necessity for the additional reagents further adds to manufacturing cost.

The instant invention has advantages when compared to the route of preparing SKA by the hydrosilation of a vinylic material, such as a methacrylate. Organosilanes, such as triorganosilanes, are not readily available in commercial quantities. A process must be established to prepare these triorganosilanes. Additionally, the starting vinylic materials are very susceptible to polymerization, and special precautions must be made to prevent vinylic polymerization during the preparation and separation of the desired SKA. Further, a by-product of the hydrosilation reaction is the carbonyl adduct,

This adduct is difficult to separate from SKA and is detrimental to the use of the SKA as an acrylate polymerization initiator, supra. The preparation of SKA via hydrosilation requires special processing steps to remove these undesirable carbonyl adducts. Additionally, many alpha-esters of carboxylic acids are commercially available or easily prepared by commercially known methods.

DESCRIPTION OF THE INVENTION

In accordance with the instant invention there is provided a process for the preparation of silyl ketene acetals (SKA) which are prepared under conditions described herein. What is described, therefore, is a process for preparing silyl ketene acetals having the formula, $$R_2C=C(OSiR_nX_{3-n})(OZ)$$

or

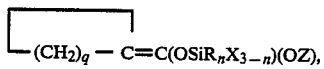

wherein each R is independently selected from a group consisting of alkyl, alkenyl, aryl, aralkyl or organosilyl; X is a halogen atom; Z is selected from a group consisting of alkyl, alkenyl, aryl, organosilyl, or haloorganosilyl; n has a value of 1, 2, or 3; and q has a value of 2 to 22, inclusive, said process comprising
(A) contacting an alpha-ester of a carboxylic acid with an alkali metal in the presence of an excess of an organohalosilane, wherein the alpha-ester has the formula,

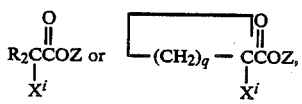

wherein the organohalosilane has the formula, $R_nSiX_{4-n}$, wherein R, X, Z, n, and q are defined above; and wherein $X^i$ is selected from a group consisting of halogen atoms and alkoxy groups; and
(B) facilitating reaction among the alpha-ester, the alkali metal, and the organohalosilane to form the silyl ketene acetal and an alkali metal halide or an alkali metal alkoxide.

The SKA may be, for example, $(CH_3)(CH_3)C=C[OSi(CH_3)_3](OCH_3)$, $(CH_3)(C_2H_5)C=C[OSi(CH_3)_3](OC_2H_5)$, $(CH_3)(CH_3)C=C[OSi(CH_3)_3](OCH_2CH=CH_2)$, $(CH_3)(C_2H_5)C=C[OSi(CH_3)_3](OC_6H_5)$, $(CH_3)(CH_3)C=C[OSi(CH_3)_3]_2$, $(CH_3)(C_2H_5)C=C[OSi(CH_3)_3]_2$, $(CH_3)(CH_2=CHCH_2)C=C[OSi(CH_3)_3](OCH_3)$, $(CH_3)(C_{10}H_{21})C=C[OSi(CH_3)_3](OCH_3)$, $(C_6H_5)(C_6H_5)C=C[OSi(CH_3)_3](OCH_3)$,

$(CH_3)(CH_3)C=C[OSi(CH_3)_2Cl](OCH_3)$, $(CH_3)(CH_3)C=C[OSi(CH_3)Br_2](OCH_3)$, $(CH_3)(CH_3)C=C[OSi(CH_3)_2(CH=CH_2)](OCH_3)$, $(CH_3)(CH_3)C=C[OSi(CH_3)_2(C_6H_5)](OCH_3)$, or $[(CH_3)_3Si](CH_3)C=C[OSi(CH_3)_3]_3)$.

The alpha-ester of a carboxylic acid can be, for example, methyl 2-chloroisobutyrate, methyl 2-bromoisobutyrate, methyl 2-chloro-2,3-dimethylisobutyrate, methyl 2-chloro-2-methylbutyrate, methyl 2-chloro-2-ethylbutyrate, ethyl 2-chloroisobutyrate, ethyl 2-chloro-2-methylbutyrate, ethyl 2-chloro-2-ethylbutyrate, methyl 2-methoxyisobutyrate, ethyl 2-ethoxy-2-methylbutyrate, allyl 2-chloroisobutyrate, phenyl 2-chloro-2-methylbutyrate,

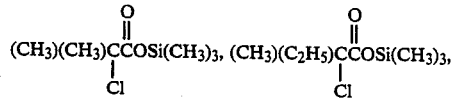

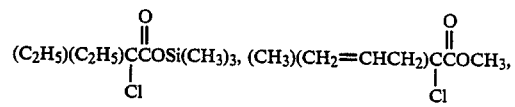

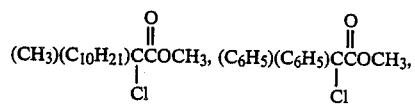

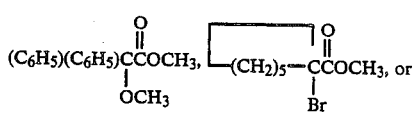

The organohalosilane may be, for example, methyltrifluorosilane, methyltrichlorosilane, dimethyldichlorosilane, trimethylchlorosilane, trimethylbromosilane, diethyldichlorosilane, triethylbromosilane, diisopropyldichlorosilane, t-butyldimethylchlorosilane, vinyltrichlorosilane, methylvinyldichlorosilane, dimethylvinylchlorosilane, phenylmethyldichlorosilane, or phenyltrichlorosilane, The alkali metal may be, for example, lithium, sodium, potassium, or alloys thereof. The preferred alkali metal is sodium. The alkali metal may be used in the form of an alloy of two or more of the metals, such as a sodium/potassium alloy in a solid or a molten form. The alkali metal may also be used in the form of a dispersion in an appropriate inert liquid, inert to the reactants or product of the instant invention, such as a paraffin. Sodium metal or an alloy of sodium metal may also be used as a dispersion of molten particles in an inert liquid.

The reaction of an alpha-ester with an alkali metal (M) in the presence of an excess of an organohalosilane can be represented by the overall reaction,

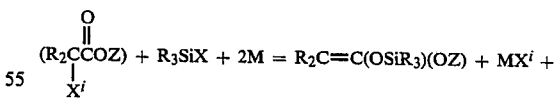

MX.

The alpha-ester and the alkali metal are thought to form an organometallic intermediate,

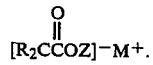

This very reactive intermediate is nearly quantitatively trapped in the presence of a sufficient excess of the organohalosilane to form the desired SKA. If the excess of the organohalosilane is not sufficient to virtually immediately trap the organometallic intermediate above, then the formation of by-products, such as those formed by acyloin condensation will occur instead.

The metal salts ($MX^i + MX$) form a large volume of fine particles which hinder reactants from contacting the surface of the metal. Dilution with excess organohalosilane or an inert liquid and agitation aid in the contact of the reactants. The rate of reaction is greatly influenced by the exposed surface of the metal and the state of the surface of the metal. Molten metal is easily dispersed in a liquid medium to present a large, highly reactive exposed area.

Contact among the reactants can occur in many modes, so long as the requirement of the presence of a sufficient excess of the organohalosilane during the reaction of the alpha-ester and the alkali metal is met. A first example of a mode of contact is the addition of all reactants to a batch reactor in a batchwise manner, the organohalosilane being present in a sufficient excess to maximize the production of SKA and to serve as a diluent for the liquid/solid mixture that results. A second example of a mode of contact is the addition of a mixture of an alpha-ester and an organohalosilane, an essentially equimolar mixture, to a mixture of an excess of the organohalosilane in an inert liquid and a molten alkali metal. A third possible mode of contact is the addition of the alpha-ester to a heated mixture of an excess of the organohalosilane and a molten alkali metal.

Contacting the alpha-ester, the organohalosilane, and the alkali metal can be carried out in a standard batch chemical reactor system. The reactor should be provided with adequate means for agitation to assure that the alkali metal is dispersed in the liquid reaction medium. For the purposes of the instant invention "facilitating reaction" means that the reactor should have provisions such as adequate agitation, heating and cooling, as necessary, and adequate liquid content to assure that the slurry formed by the liquid reactants and products and solid alkali halide salts is a manageable physical mixture.

The presence of adequate liquid to assure that the mixture of reactants, product, and solid salt is a manageable physical mixture to allow sufficient contact among the reactants can be facilitated by using excess organohalosilane ae a diluent. Additionally an inert liquid, inert to the reactants and product, may be utilized as a diluent. Examples of such inert liquids are aliphatic hydrocarbons, ethers, aromatic hydrocarbons, and mineral oils.

As outlined, supra, the overall stoichiometric amount of the organohalosilane relative to the alpha-ester is 1.0:1. Also, as noted supra, the presence of a sufficient excess of the organohalosilane is necessary to maximize the yield of SKA. In a batch mode in which all reactants are contacted simultaneously, the molar ratio of the organohalosilane relative to the alpha-ester should be greater than about 2.0:1, a stoichiometric excess of greater than about 100 percent. Preferably this molar ratio should be in a range of from about 100 to 400 percent. It is understood that less than a 100 percent stoichiometric excess may be utilized; however, problems such as a very heavy slurry of the liquids and solids of reaction may result causing appendant processing problems. Molar excesses of the organohalosilane greater than those disclosed above may be utilized; however, the inventor believes that no further benefit will be realized in the use cf such excesses.

In a contact mode in which a mixture of an alpha-ester and an organohalosilane are added to a mixture of the organohalosilane and a molten alkali metal, the alpha-ester and the alkali metal react very rapidly and the organometallic intermediate formed rapidly reacts with the excess organohalosilane to form SKA. The excess organohalosilane in the reactor is replenished by the organohalosilane added with the alpha-ester. The inventors believe that an overall excess of the organohalosilane of greater than about 10 percent on a molar basis relative to the alpha-ester is a sufficient excess to effect maximum conversion of the alpha-ester to SKA.

As outlined, supra, the overall stoichiometric amount of the alkali metal relative to the alpha-ester is 2.0:1. The inventors believe that a stoichiometric excess as low as 5 percent or 2.10:1 is sufficient to essentially convert all of the alpha-ester to SKA. However, the amount of alkali metal relative to the alpha-ester is not critical, provided an excess of organohalosilane relative to the alpha-ester exists. Less than the stoichiometric excess of the alkali metal would result in unreacted alpha-ester, which could be separated from the desired SKA.

When an inert liquid, in addition to the organohalosilane, is utilized, the stoichiometric excess of the organohalosilane can be reduced proportionately to the level sufficient to maximize conversion of the alpha-ester, as outlined supra.

The temperature of contact among the reactants affects reaction rate. However, as noted supra, the degree of conversion of the alpha-ester to SKA is a function of a sufficient excess of the organohalosilane. Temperature does have an impact when it is desired to maintain the alkali metal or alkali metal alloy in a molten state. Temperature of contact can be affected by the addition of an inert liquid or the application of pressure to raise the temperature to which the liquid mixture can be heated. As an example, contact and reaction can be carried out at temperatures from ambient up to the atmospheric boiling or refluxing temperature of the organohalosilane; trimethylchlorosilane at refluxing conditions will set temperature at greater than about 50° C. A mixture of an inert liquid and an organohalosilane can be utilized to set the temperature above the melting point of the alkali metal; for example, a mixture of octane and trimethylchlorosilane can be proportioned to provide a reflux temperature greater than the melting point of sodium (97.5° C.).

The time required to complete the process is established by the temperature of the reaction mixture and the form of the alkali metal. For example, using trimethylchlorosilane as both a reactant and a solvent, and chunks of solid sodium metal, liquid temperature at reflux is about 50° to 60° C.; and needed time to effect essentially complete reaction of the alpha-ester is greater than 2 hours, and often greater than about 10 hours. As a further example, a mixture of octane and trimethylchlorosilane can be made with a boiling point of about 105° C. to provide molten sodium in the reaction mixture. Under these latter conditions, time for essentially complete consumption of the alpha-ester is 1 hour or less.

The process of the instant invention can further comprise isolating and separating the SKA. Separating and isolating the SKA can be effected by distillation of the SKA from the liquid/solid mixture. More preferably, separating and isolating the SKA comprises removing alkali halide or alkali alkoxide solids first, and then recovering the SKA by distillation. The alkali halide or alkali alkoxide salts are generated at a volume of 2 moles per mole of SKA. These salts may be removed by such known techniques as filtration of the salts from the crude product mixture. Any commercial filtration method such as pressure filtration can be utilized.

Recovery of the desired SKA from the crude product mixture, before or after removal of salts, can be effected by such known techniques as distillation. It has been shown in the examples, infra, that SKA prepared by the process of the instant invention can be recovered by distillation to purities of at least 90 weight percent. Further, the excess organohalosilane can also be isolated and separated by distillation, facilitating possible recycle back to the process.

So that those skilled in the art may better understand the instant invention, the following examples are presented. The examples are presented as being illustrative and are not to be construed as limiting the instant invention as delineated in the claims.

EXAMPLE 1

A silyl ketene acetal (SKA) was prepared from the reaction of an alpha-haloester of a carboxylic acid, an alkali metal, and an organohalosilane. The synthesis and analytical procedures followed to prepare the crude reaction mixture in this example are typical of those utilized in the subsequent examples.

Into a 100-ml, three-necked flask, fitted with a mechanical agitator and a reflux condenser was added 10 g (0.0733 mole) of methyl 2-chloroisobutyrate, 40 g (0.37 mole) of trimethylchlorosilane, and 3.8 g (0.165 g-atom) of sodium. The sodium was added as 0.1–0.5 g pieces. The flask had been purged with nitrogen and purging was continued throughout the course of the reaction. The above mixture was heated to reflux for 20 hours. A sample of the liquid was taken and analyzed with a capillary gas chromatograph with a flame ionization detector. The analysis showed approximately 94 percent conversion of the alpha-chloroester and showed that of the alpha-chloroester consumed, 96.3 percent was converted to the SKA.

$(CH_3)_2C=C[OSi(CH_3)_3](OCH_3)$,

A second sample was taken after a total of 40 hours at reflux. Analysis showed that greater than 96 percent of the chloroester had been consumed and showed that the SKA yield was 96.8 percent.

The methyl 2-chloroisobutyrate was prepared by a known alkylation reaction. In this synthesis diisopropylamine in a tetrahydrofuran (THF) solution is reacted with a hexane solution of n-butyllithium at a low temperature. Next a commercially available alpha-haloester, methyl 2-chloropropionate, was added to this cooled solution. Once this addition is completed, a commercially available alkyl halide, methyl iodide, was added and salts were washed from the resulting mixture. The organic mixture was neutralized with an aqueous neutralizing agent and then dried. The desired final alpha-haloester was recovered by vacuum distillation.

The above results show that high yields of a SKA can be prepared from the reaction of an alpha-chloroester with an alkali metal and an excess of an organochlorosilane.

EXAMPLE 2

Using the apparatus and procedures described in Example 1, 10 g (0.038 mole) of methyl 2-chloro-2-methyldodecanoate, 20.6 g (0.190 mole) of trimethylchlorosilane, and 1.97 g (0.0855 g-atom) of sodium were placed in the flask and heated to reflux for 40 hours. After this time analysis showed that the conversion of the chloroester was 98.6 percent. Analysis further indicated that of the chloroester consumed, 92.9 percent had been converted to SKA, $(CH_3)(C_{10}H_{21})C=C[OSi(CH_3)_3](OCH_3)$.

Solid sodium chloride was separated from the liquid in the mixture by a standard vacuum filtration technique. The solids-free liquid mixture was distilled in a standard distillation apparatus, fitted for vacuum operation. The product was taken overhead at a temperature of 129°–130° C. at a pressure of 0.5 mm Hg. A total of 9.1 g of product was collected for a yield of 79.8 percent, based upon the starting chloroester.

The methyl 2-chloro-2-methyldodecanoate was prepared by a known alkylation reaction, as described in Example 1. Commercially available methyl 2-chloropropionate and n-bromodecane were reactants utilized.

The above results demonstrate that SKA can be prepared and recovered in high yield from the reaction of an alphachloroester, an alkali metal, and an organochlorosilane.

EXAMPLE 3

Using the apparatus and techniques utilized in Examples 1 and 2, several SKA having the formula, $R^1R^2C=C[OSi(CH_3)_3](OR^3)$, are prepared from the reaction of an alpha-haloester of a carboxylic acid having the formula, $$R^1R^2\underset{X^i}{\overset{O}{\underset{|}{C}}}COR^3,$$

with sodium and excess trimethylchlorosilane.

The specific alpha-haloester, the sodium, and the trimethylchlorosilane were contacted at a molar ratio of 1:2.25:5.0 in all cases.

Table 1 is a summary of the alpha-ester/organohalosilane combinations evaluated. These runs are identified as Samples A through M, respectively. These samples are identified in Table 1 by organic groups, designated "$R^1$", "$R^2$", and "$R^3$"; and halogen atom or alkoxy group, designated "X". Further, Table 1 summarizes the percent conversion of the alpha-ester, designated as "% Conv"; and the percentage of the alpha-ester consumed that is present as SKA, designated as "% Yield".

TABLE 1

| Sample | $R^1$ | $R^2$ | $R^3$ | X | % Conv | % Yield |
|---|---|---|---|---|---|---|
| A | $CH_3$ | $C_2H_5$ | $CH_3$ | Cl | 97.4 | 87.6 |
| B | $CH_3$ | $i\text{-}C_3H_7$ | $CH_3$ | Cl | 93.0 | 80.4 |
| C | $CH_3$ | $CH_2=CHCH_2$ | $CH_3$ | Cl | 95.4 | 78.1 |
| D | $CH_3$ | $C_6H_5$ | $CH_3$ | Cl | 93.1 | 94.7 |
| E | $CH_3$ | $CH_3$ | $C_2H_5$ | Cl | 99.0 | 93.6 |
| F | $CH_3$ | $C_2H_5$ | $C_2H_5$ | Cl | 97.7 | 87.0 |

TABLE 1-continued

| Sample | R$^1$ | R$^2$ | R$^3$ | X | % Conv | % Yield |
|---|---|---|---|---|---|---|
| G | CH$_3$ | CH$_3$ | (CH$_3$)$_3$Si | Br | 98.6 | 92.8 |
| H | C$_6$H$_5$ | CH$_3$ | CH$_3$ | Cl | 92.6 | 61.9 |
| I | C$_6$H$_5$ | C$_6$H$_5$CH$_2$ | CH$_3$ | Cl | 91.8 | 94.9 |
| J | CH$_3$ | CH$_3$ | C$_2$H$_5$ | Br | 97.1 | 88.4 |
| K | C$_6$H$_5$ | C$_6$H$_5$ | CH$_3$ | Cl | 61.0 | 12.5 |
| L | —(CH$_2$)$_5$— | | CH$_3$ | Br | 99.5 | 88.8 |
| M | C$_6$H$_5$ | C$_6$H$_5$ | CH$_3$ | OCH$_3$ | 30.9 | 15.8 |

The ethyl 2-bromoisobutyrate used in the preparation of Sample J is a commercially available material.

The alpha-haloesters utilized in the preparation of Samples A, B, C, D, E, F, H, and I, respectively, were prepared by a known alkylation reaction which is described in Example 1.

The trimethylsilyl 2-bromoisobutyrate used in the preparation of Sample G was prepared by a known silylation method, 2-bromoisobutyric acid, prepared by Lancaster Synthesis, was reacted with trimethylchlorosilane forming the desired silyl haloester and hydrogen chloride. The desired product was recovered by vacuum distillation. The product was taken off at an overhead temperature of 52°–53° C. at a pressure of 12 mm Hg.

The alpha-haloesters used to produce Samples K and M were prepared by reaction of the corresponding carbonyl chloride with an alcohol. As an example, 2-chloro-2-phenylacetyl chloride was reacted with anhydrous methanol overnight at reflux. Volatiles were removed in a rotary evaporator at about 40° C. at water aspirator vacuum. The residue was distilled to give an overhead product at a temperature of 86°–87° C. at a pressure of 0.5 mm Hg.

The methyl 2-bromocyclohexanecarboxylate utilized in the preparation of Sample L was prepared from the reaction of cyclohexanecarboxylic acid and bromine in 1,2-dichloroethane in the presence of chlorosulfonic acid. The mixture was heated to reflux with agitation. Reflux at a temperature of about 80° C. was continued for about 16 hours. Bromine and dichloroethane were distilled at atmospheric pressure. Methanol was added and the system heated to reflux for about 20 hours. The system was again distilled at atmospheric pressure. The residue was washed with water and aqueous sodium bicarbonate. Dichloroethane was used to aid in dissolving any solids that were formed. The organic phase was dried over sodium sulfate and filtered. The bulk of the dichloroethane was removed by stripping under aspirator vacuum. The final product was distilled as an overhead material at a temperature of 72°–74° C. at a pressure of 0.5 mm Hg.

The above results demonstrate that a wide range of SKA can be produced by the process of the instant invention.

EXAMPLE 4

A run was made at a temperature above the melting point of sodium (97.5° C.). This procedure resulted in a fine dispersion of molten sodium in the liquid reaction medium.

Into a 1000-ml vessel, equipped with agitator, reflux condenser, and addition funnel was added 250 g of octane and 26.6 g (1.16 gram-atoms) of sodium. The octane and sodium were heated to the boiling point of octane (125.7° C.) and allowed to reflux, thereby melting the sodium. Trimethylchlorosilane was added to the refluxing mixture to lower the boiling point of the liquid medium to about 105° C. This took about 47 g (ca. 0.44 mole) of trimethylchlorosilane. Immediately thereafter, the dropwise addition of a 1:1 molar mixture of trimethylchlorosilane and methyl 2-bromoisobutyrate was begun. Over a 45 minute period, a total of 60 g trimethylchlorosilane and 100 g methyl 2-bromoisobutyrate, 0.55 mole of each, were added to the refluxing mixture. After the addition of this mixture was completed, the mixture was held at reflux for an additional 15 minutes. The mixture was cooled, and a sample of the liquid portion of the reaction mixture was analyzed via gas chromatographic technique.

By gas chromatographic area percent, the conversion of the starting methyl 2-bromoisobutyrate was determined to be 96.0 percent. Of the methyl 2-bromoisobutyrate converted, it was determined that 94.2 percent was converted to the desired silyl ketene acetal,

(CH$_3$)$_2$C=C[OSi(CH$_3$)$_3$](OCH$_3$),

The above results demonstrate that dispersed molten sodium significantly shortens the time required to convert an alpha-haloester to the desired SKA.

EXAMPLE 5

A run was made in which a molten 70:30 (by weight) sodium:potassium alloy, with a melting point of about 50° C., was used for the preparation of SKA, The sodium:potassium alloy was prepared by mashing 2.66 g (0.116 g-at) sodium with 1.14 g (0.029 g-at) potassium and adding the combined metals to refluxing hexane. The hexane mixture with the metals was cooled, and the hexane was removed with a pipette.

A total of 30.0 g (0.276 g-mol) trimethylchlorosilane was slowly added to the alloy. Contact of the trimethylchlorosilane with the alloy caused significant generation of heat and foaming. The trimethylchlorosilane and alloy were heated to about 50° C. Methyl 2-bromoisobutyrate was added slowly to the mixture of trimethylchlorosilane and the alloy. After the first few drops of the alpha-bromoester was added, the alloy melted and the reaction mixture heated to vigorous reflux and was maintained there via the rate of addition of the bromoester. A total of 10.0 g (0.055 g-mol) of the methyl 2-bromoisobutyrate was added over a period of about 20 minutes. The reaction mixture was held at reflux for an additional 20 minutes and sampled. Analysis by GC and a combination GC/mass spectrographic technique showed that the conversion of the methyl 2-bromoisobutyrate was 94.8 percent and that 97.3 percent of the bromoester converted yielded the SKA,

(CH$_3$)$_2$C=C[OSi(CH$_3$)$_3$](OCH$_3$).

The above results further demonstrate that a molten alkali metal or an alloy of alkali metals greatly reduces the time required for the preparation of silyl ketene acetals from alpha-haloesters.

EXAMPLE 6

(Not within the scope of the instant invention)

Using the procedures and analytical techniques utilized in Examples 1 and 2, the reaction of ethyl 2-bromopropionate with trimethylchlorosilane in the presence of sodium was studied. The reaction mixture consisted of 1 equivalent of the ethyl 2-bromopropionate, 2 equivalents of sodium, and 5 equivalents of trimethylchlorosilane. The reaction was run over 40 hours at reflux.

The final product composition was analyzed by gas chromatography. The results showed that the final product was 22.6 percent ethyl 2-bromopropionate, 40.2 percent of the SKA, $(CH_3)HC=C[OSi(CH_3)_3](OC_2H_5)$, and 37.2 percent of minor products. These minor products were identified as C-silylated ester, acyloin condensation products, and unidentified materials.

The above result demonstrates that the use of an alpha-haloester in which the halogen atom is bonded to a *secondary* carbon atom does not result in high yields of the desired SKA as does reaction of the alpha-haloester in which the halogen atom is bonded to a *tertiary* carbon atom.

What is claimed is:

1. A process for preparing silyl ketene acetals having the formula, $$R_2C=C(OSiR_{3-n}X_n)(OZ)$$

or $$\underline{\hspace{0.3cm}}(CH_2)_q - C=C(OSiR_nX_{3-n})(OZ),$$

wherein each R is independently selected from a group consisting of alkyl, alkenyl, aryl, aralkyl, or organosilyl; X is a halogen atom; Z is selected from a group consisting of alkyl, alkenyl, aryl, organosilyl, or haloorganosilyl; n has a value of 1, 2, or 3; and q has a value of 2 to 22, inclusive, said process comprising (A) contacting an alpha-ester of a carboxylic acid with an alkali metal in the presence of an excess of an organohalosilane, wherein the alpha-ester has the formula, $$R_2\underset{X^i}{\overset{O}{\overset{\|}{C}}}COZ \quad \text{or} \quad \underline{\hspace{0.3cm}}(CH_2)_q - \underset{X^i}{\overset{O}{\overset{\|}{C}}}COZ,$$

wherein the organohalosilane has the formula, $$R_nSiX_{4-n},$$

wherein R, X, Z, n, and q are defined above; and wherein $X^i$ is selected from a group consisting of halogen atoms and alkoxy groups; and (B) facilitating reaction among the alpha-ester, the alkali metal, and the organohalosilane to form the silyl ketene acetal and an alkali metal halide of an alkali metal alkoxide.

2. A process according to claim 1, wherein the alkali metal is in a stoichiometric excess relative to the alpha-ester.

3. A process according to claim 1, wherein the alkali metal is selected from a group consisting of lithium, sodium, potassium, and alloys thereof.

4. A process according to claim 3, wherein the alkali metal is in the form selected from a group consisting of solid metal, solid metal in a dispersion in an inert liquid, molten metal, and molten metal in an inert liquid.

5. A process according to claim 1, further comprising isolating and separating the silyl ketene acetal.

6. A process according to claim 5, wherein isolating and separating the silyl ketene acetal comprises distillation.

7. A process according to claim 6, wherein isolating and separating the silyl ketene acetal further comprises removal of the alkali metal salts prior to distillation.

8. A process according to claim 1, wherein the alpha-ester is an alpha-haloester; wherein the alkali metal is solid sodium; wherein the organohalosilane is trimethylchlorosilane; wherein the sodium is present in a stoichiometric excess of greater than about 5 percent and the trimethylchlorosilane is present at a stoichiometric excess in a range from about 100 to 400 percent, said stoichiometric excesses being relative to the alpha-haloester; wherein the alpha-haloester, the sodium, and the trimethylchlorosilane are contacted simultaneously in a batchwise manner; wherein sodium chloride is removed by filtration; and wherein the silyl ketene acetal is separated and isolated by distillation at a purity of greater than about 90 weight percent.

9. A process according to claim 8, wherein the alpha-haloester is methyl 2-chloroisobutyrate; and wherein the silyl ketene acetal is $$(CH_3)(CH_3)C=C[OSi(CH_3)_3](OCH_3).$$

10. A process according to claim 8, wherein the alpha-haloester is methyl 2-chloro-2-methylbutyrate; and wherein the silyl ketene acetal is $$(CH_3)(C_2H_5)C=C[OSi(CH_3)_3](OCH_3).$$

11. A process according to claim 8, wherein the alpha-haloester is methyl 2-chloro-2,3,-dimethylbutyrate; and wherein the silyl ketene acetal is $$(CH_3)(i-C_3H_7)C=C[OSi(CH_3)_3](OCH_3).$$

12. A process according to claim 8, wherein the alpha-haloester is $$(CH_3)(CH_2=CHCH_2)\underset{Cl}{\overset{O}{\overset{\|}{C}}}COCH_3;$$

and wherein the silyl ketene acetal is $$(CH_3)(CH_2=CHCH_2)C=C[OSi(CH_3)_3](OCH_3).$$

13. A process according to claim 8, wherein the alpha-haloester is $$(CH_3)(C_6H_5)\underset{Cl}{\overset{O}{\overset{\|}{C}}}COCH_3;$$

and wherein the silyl ketene acetal is $$(CH_3)(C_6H_5)C=C[OSi(CH_3)_3](OCH_3).$$

14. A process according to claim 8, wherein the alpha-haloester is $$(CH_3)(CH_3)\underset{Br}{\overset{O}{\overset{\|}{C}}}COSi(CH_3)_3;$$

and wherein the silyl ketene acetal is $$(CH_3)(CH_3)C=C[OSi(CH_3)_3]_2.$$

15. A process according to claim 8, wherein the alpha-haloester is

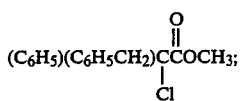

and wherein the silyl ketene acetal is $(C_6H_5)(C_6H_5CH_2)C=C[OSi(CH_3)_3](OCH_3)$.

16. A process according to claim 8, wherein the alpha-haloester is

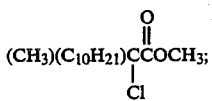

and wherein the silyl ketene acetal is $(CH_3)(C_{10}H_{21})C=C[OSi(CH_3)_3](OCH_3)$.

17. A process according to claim 8, wherein the alpha-haloester is

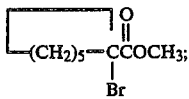

and wherein the silyl ketene acetal is

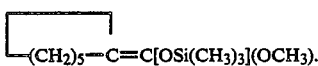

18. A process according to claim 1, wherein a mixture of an alpha-ester and a first portion of the organohalosilane, said first portion of the organohalosilane being present in a molar proportion essentially equal to the alpha-ester, is added to a dispersion of a molten alkali metal in an inert liquid and a second portion of the organohalosilane; wherein the proportions of the inert liquid and second portion of the organohalosilane in the dispersion are controlled so that the temperature of the dispersion is above the melting point of the alkali metal.

19. A process according to claim 18, wherein the alkali metal is sodium; wherein the organohalosilane is trimethylchlorosilane; wherein the inert liquid is octane; wherein sodium halide is removed by filtration; and wherein the silyl ketene acetal is separated and isolated by distillation to a purity greater than about 90 weight percent.

20. A process according to claim 19, wherein the alpha-ester is methyl 2-bromoisobutyrate; and wherein the silyl ketene acetal is $(CH_3)(CH_3)C=C[OSi(CH_3)_3](OCH_3)$.

21. A process according to claim 1, wherein the alkali metal is molten; wherein the alpha-ester is added to a mixture of the molten alkali metal and the organohalosilane; wherein temperature is controlled to maintain the alkali metal in a molten state.

22. A process according to claim 21, wherein the alkali metal is an alloy of sodium and potassium; wherein the organohalosilane is trimethylchlorosilane; wherein sodium halide and potassium halide are removed by filtration; and wherein the silyl ketene acetal is separated and isolated by distillation to a purity greater than about 90 weight percent.

23. A process according to claim 22, wherein the alpha-ester is methyl 2-bromoisobutyrate; and wherein the silyl ketene acetal is $(CH_3)(CH_3)C=C[OSi(CH_3)_3](OCH_3)$.

* * * * *

UNITED STATES PATENT AND TRADEMARK OFFICE
CERTIFICATE OF CORRECTION

PATENT NO. : 4,783,543
DATED : November 8, 1988
INVENTOR(S) : WILLIAM J. SCHULZ, JR., JOHN L. SPEIER It is certified that error appears in the above-identified patent and that said Letters Patent is hereby corrected as shown below:

COLUMN 13, LINE 20 - SHOULD READ $R_2C=C(OSiR_nX_{3-n})(OZ)$
INSTEAD OF $R_2C=C(OSiR_{3-n}X_n)(OZ)$

Signed and Sealed this

Twelfth Day of October, 1993

Attest:

BRUCE LEHMAN

Attesting Officer

Commissioner of Patents and Trademarks